(12) United States Patent
Sperl et al.

(10) Patent No.: US 7,608,623 B2
(45) Date of Patent: Oct. 27, 2009

(54) HYDROXYAMIDINE AND HYDROXYGUANIDINE COMPOUNDS AS UROKINASE INHIBITORS

(75) Inventors: Stefan Sperl, Munich (DE); Markus Buergle, Munich (DE); Wolfgang Schmalix, Groebenzell (DE); Katja Wosikowski, Poing (DE); Bernd Clement, Kiel (DE)

(73) Assignee: Wilex AG, Munich (DE)

( * ) Notice: Subject to any disclaimer, the term of this patent is extended or adjusted under 35 U.S.C. 154(b) by 174 days.

(21) Appl. No.: 11/287,480

(22) Filed: Nov. 28, 2005

(65) Prior Publication Data
US 2006/0142305 A1 Jun. 29, 2006

Related U.S. Application Data

(63) Continuation-in-part of application No. PCT/EP2004/005682, filed on May 26, 2004.

(30) Foreign Application Priority Data

May 26, 2003 (DE) .............................. 103 23 898

(51) Int. Cl.
*A61K 31/4965* (2006.01)
(52) U.S. Cl. .................................. 514/255.01
(58) Field of Classification Search ........................ None
See application file for complete search history.

(56) References Cited

U.S. PATENT DOCUMENTS 7,211,670 B2   5/2007   Ag

FOREIGN PATENT DOCUMENTS

WO   WO/03072559   *   9/2003

OTHER PUBLICATIONS

Cecil Textbook of Medicine, 21th Edition (2001), Goldman & Bennett (Editors), W.B. Saunders Company (Publisher), Chapter 198, Principles of Cancer Therpay, pp. 1060-1074.*
Http://www.healthline.com/galecontent/giant-cell-tumors. Accessed Aug. 2007.*

* cited by examiner

*Primary Examiner*—James O Wilson
*Assistant Examiner*—Jeffrey H Murray
(74) *Attorney, Agent, or Firm*—Rothwell, Figg, Ernst & Manbeck, P.C.

(57) ABSTRACT

The present invention relates to novel compounds for inhibiting the urokinase plasminogen activator (uPA), which have high bioavailability and oral administerability, and also to the use thereof as therapeutic active compounds for the treatment of urokinase- or/and urokinase receptor-associated disorders such as, for example, tumors and metastasizing. The invention relates in particular to compounds containing hydroxyamidine or hydroxyguanidine groups.

6 Claims, 10 Drawing Sheets

HYDROXYAMIDINE AND HYDROXYGUANIDINE COMPOUNDS AS UROKINASE INHIBITORS

CROSS REFERENCE TO RELATED APPLICATION

This application is a continuation-in-part of PCT/EP04/05682, filed May 26, 2004, which claims the benefit of priority to DE 103 23 898.0, filed May 26, 2003, the contents of which are hereby incorporated by reference.

BACKGROUND

The present invention relates to novel compounds for inhibiting the urokinase plasminogen activator (uPA), which have high bioavailability and oral administerability, and also to the use thereof as therapeutic active compounds for the treatment of urokinase- or/and urokinase receptor-associated disorders such as, for example, tumors and metastasizing. The invention relates in particular to compounds containing hydroxyamidine or hydroxyguanidine groups.

The plasminogen activator of the urokinase type (uPA) plays a key part in tumor invasion and the formation of metastases (Schmitt et al., J. Obst. Gyn. 21 (1995), 151-165). uPA is expressed in many different types of tumor cells (Kwaan, Cancer Metastasis Rev. 11 (1992), 291-311) and binds to the tumor-associated uPA receptor (uPAR) where activation of plasminogen to plasmin occurs. Plasmin is capable of degrading various components of the extracellular matrix (ECM), such as fibronectin, laminin and type IV collagen. It also activates some other ECM-degrading enzymes, in particular matrix metalloproteinases. Large amounts of tumor-associated uPA correlate with a higher risk of metastasizing for cancer patients (Harbeck et al., Cancer Research 62 (2002), 4617-4622). Inhibition of the proteolytic activity of uPA is therefore a good starting point for an antimetastatic therapy.

Some active and selective urokinase inhibitors have been described previously. Thus, EP 1 098 651 discloses benzamidine-type uPA inhibitors, and WO 01/96286 and WO 02/14349 disclose arylguanidine-type uPA inhibitors. A common feature of these synthetic inhibitors is a basic radical consisting of an amidino or/and guanidino group.

However, the known urokinase inhibitors have the disadvantage of being absorbed poorly when applied orally and thus can exert only a low pharmacological action in the body with this type of administration. Pharmaceutical preparations are therefore administered to the patient intravenously usually once, but up to twice weekly over a period of several hours. This puts a great strain on the patient, since this requires considerable time and frequent hospital visits and demands a high level of cooperation of the patient.

Moreover, intravenous administration carries the risk of infections and, especially in the case of paravasally escaping infusate, severe local irritations up to tissue necroses may occur, which require time-consuming subsequent treatments and monitoring.

Intramuscular and subcutaneous routes of administration also do not offer any advantages, since here frequently severe pain at the injection sites and also irritations up to tissue necroses may occur, which likewise require a time-consuming after-treatment.

As discussed above, the amidine- and guanidine-containing urokinase inhibitors exhibit only low pharmacological action when applied orally. A precondition for the therapeutic effect of an active compound is the bioavailability of the latter. Oral administration requires absorption from the gastrointestinal tract. An important mechanism of this kind of membrane penetration is passive diffusion (Gangvar S. et al., DDT (1997) 148-155). The lipophilicity of an active compound was assumed in some parts of the literature to play an important part in passive diffusion via the membrane barriers of the gastrointestinal tract. Thus, EP 0 708 640 describes for pentamidines with antihelminthic action a modification of amidine functions to give amidoxime, amidoxime ester and oxadiazole, with preference being given to using the amidoxime esters and oxadiazole as suitable modifications.

On the other hand, however, it was shown that the degree of lipophilicity alone is not sufficient (Hansch et al., J. Am. Chem. Soc. 86 (1964) 1616-1626) and that an increase in the lipophilicity of the compounds is not an appropriate parameter for predicting membrane penetration. Thus, a direct relation between lipophilicity and membrane. permeation was not found (Conradi et al., Pharm. Res. 9 (1992) 435-439).

The increase in lipophilicity may therefore, in individual cases, increase membrane permeation, but not necessarily lead to an increased oral bioavailability. Thus, in the case of argatroban, conversion of the basic radical to the amidoxime as a prodrug results in improved permeability but, in addition, in the loss of activity (Rewinkel, Adang Cur. Pharm. Design 5 (1999) 1043-1075). It is therefore not readily predictable, whether and which modifications can improve membrane penetration of an active compound in the gastrointestinal tract. It is even less predictable which influence said modifications may have on the pharmaceutical properties of the active compound.

BRIEF SUMMARY OF THE INVENTION

It was an object of the present invention to provide novel medicaments for inhibiting urokinase, whose bio-availability and activity in the organism, in the case of oral administration, is distinctly increased.

According to the invention, this object is achieved by a medicament, which comprises, as an active compound, one or more compounds of the general formula I and/or II

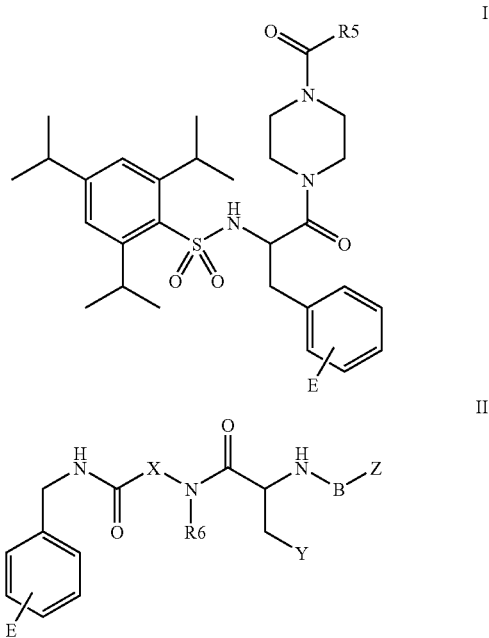

in which
E is a group from

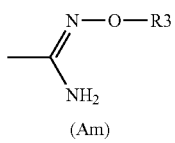 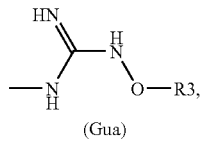
(Am)                  (Gua)

B is —SO$_2$— or —CO—,
X is —NR$^1$ or —CHR$^1$,
Z is —R$^4$, —OR$^4$ or —NH—R$^4$,
Y is —OR$^2$ or —NHR$^2$,
R$^1$ is in each case independently —H, —C$_1$-C$_6$-alkyl, —C$_2$-C$_6$-alkenyl or —C$_2$-C$_6$-alkynyl, unsubstituted or substituted,
R$^2$ is —H, —OR$^1$, —COR$^1$, —COOR$^1$ or —CON(R$^1$)$_2$,
R$^3$ is —H, —C$_1$-C$_6$-alkyl, —C$_2$-C$_6$-alkenyl or —C$_2$-C$_6$-alkynyl, unsubstituted or substituted, or —COR$^6$ or —COOR$^6$ or an oligo- or polyalkyleneoxy radical, for example with 2-50—C$_2$-C$_4$-alkyleneoxy, for example ethyleneoxy, radicals,
R$^4$ is —H, —C$_1$-C$_6$-alkyl, —C$_2$-C$_6$-alkenyl or —C$_2$-C$_6$-alkynyl, unsubstituted or substituted, or a cyclic radical, and
R$^5$ is —OR$^6$, —N(R$^6$)$_2$, —C$_1$-C$_6$-alkyl, —C$_2$-C$_6$-alkenyl or —C$_2$-C$_6$-alkynyl, unsubstituted or substituted, and
R$^6$ is —H, —C$_1$-C$_6$-alkyl, —C$_2$-C$_6$-alkenyl or —C$_2$-C$_6$-alkynyl, unsubstituted or substituted, or a cyclic radical, with each cyclic radical being able to carry one or more substituents, for example selected from the group consisting of —C$_1$-C$_3$-alkyl, —OR$^6$(e.g. —OH or —C$_1$-C$_3$-alkoxy), hydrogen, =O, —NO$_2$, —CN, —COOR$^6$, —N(R$^6$)$_2$, —NR$^6$COR$^6$, —NR$^6$CON(R$^6$)$_2$ and —OCOR$^6$, and it being possible for each alkyl, alkenyl or alkynyl to be straight-chained or branched and to carry one or more substituents, for example selected from the group consisting of halogen (F, Cl, Br, I), —OR$^6$, —OCOR$^6$, —N(R$^6$)$_2$, —NR$^6$COR$^6$, COOR$^6$, —NR$^6$COR$^6$ or a cyclic radical, or salts of said compounds and, where appropriate, pharmaceutically customary carriers, diluents or/and excipients.

The medicament is preferably an orally administrable agent. Particular preference is given to using the medicament for inhibiting the urokinase plasminogen activator.

Preference is given to compounds of the general formula III

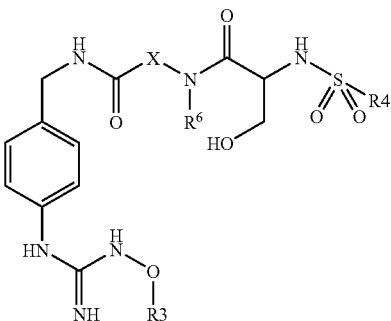

in which
X, R$^1$, R$^3$, R$^4$ and R$^6$ are defined as above,
or salts thereof.

The group E is preferably located in the para position of the phenyl ring in compounds I and II. Particular preference is given to compounds of the general formula I, in which E is Am.

The compounds of the invention have a modified amidino or guanidino function E, preferably a hydroxyguanidino or hydroxyamidino function. Such modifications have been known only as synthetic intermediates in the preparation of urokinase inhibitors of the guanidino or amidino type. A pharmaceutical effectiveness has not been suspected previously.

The compounds may be in the form of salts, preferably physiologically compatible acid salts, for example salts of mineral acids, particularly preferably hydrochlorides or hydrogen sulfates, or in the form of salts of suitable organic acids, for example of organic carboxylic or sulfonic acids, such as, for example, tartrates, mesylates or besylates. Particular preference is given to hydrogen sulfates. The compounds may be in the form of optically pure compounds or in the form of mixtures of enantiomers or/and diastereomers.

Cyclic radicals may contain one or more saturated, unsaturated or aromatic rings. Preferred examples of cyclic radicals are cycloalkyl radicals, aryl radicals, heteroaryl radicals and bicyclic radicals. Particular preference is given to mono- or bicyclic radicals. The cyclic radicals preferably contain from 4 to 30, in particular 5-10, carbon and heteroatoms as ring atoms, and also optionally one or more substituents, as indicated above. Heterocyclic systems preferably contain one or more O, S or/and N atoms. Preference is given to those bicyclic ring systems having a —CO— radical.

Alkyl, alkenyl and alkynyl groups preferably contain up to 4 carbon atoms. R$^1$ is preferably hydrogen or an optionally substituted C$_1$-C$_4$-alkyl radical, for example —CH$_3$ or a C$_1$-C$_6$-alkyl-aryl radical, so that —CO—X—NR$^1$ may be, for example, a glycyl, alanyl, phenylalanyl or homophenylalanyl radical. R$^2$ is particularly preferably hydrogen or a C$_1$-C$_3$-alkyl radical so that Y may be, for example, an OH or O—C$_1$-C$_3$-alkyl radical. R$^3$ is particularly preferably hydrogen. R$^5$ in compounds I preferably means —NHR$^6$, particularly preferably —NH(C$_1$-C$_5$)alkyl, unsubstituted or substituted, for example —NHC$_2$H$_5$ or —OR$^6$, particularly preferably —O(C$_1$-C$_3$)alkyl, unsubstituted or substituted, for example ethyloxy or benzyloxy, or —O-aryl, for example phenyloxy. R$^6$ in the compounds II and III is preferably —H or C$_1$-C$_3$-alkyl.

Preference is given to compounds in which the structural element Z is R$^4$ which is an alkyl radical having a cyclic substituent, for example an optionally substituted phenyl radical or a bicyclic radical such as, for example,

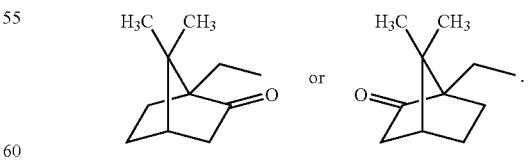

Particular preference is given to those compounds in which R$^4$ is a substituted or unsubstituted C$_1$-C$_3$-alkyl-aryl radical, for example a benzyl radical, which may be optionally substituted in the meta or para position with halogen or/and —NO$_2$, said halogen being selected from the group consisting of F, Cl, Br and I, particularly preferably Cl and Br.

Most preference is given to the compounds

N-α-(2,4,6-triisopropylphenylsulfonyl)-3-hydroxyamidino-(L)-phenylalanine-4-ethoxycarbonylpiperazide (WX-671), N-α-(2,4,6-triisopropylphenylsulfonyl)-3-hydroxyamidino-(D)-phenylalanine-4-ethoxycarbonylpiperazide, N-α-(2,4,6-triisopropylphenylsulfonyl)-3-hydroxyamidino-(D,L)-phenylalanine-4-ethoxycarbonylpiperazide, N-α-(2,4,6-triisopropylphenylsulfonyl)-3-hydroxyguanidino-(L)-phenylalanine-4-ethoxycarbonylpiperazide (WX-683), N-α-(2,4,6-triisopropylphenylsulfonyl)-3-hydroxyguanidino-(D)-phenylalanine-4-ethoxycarbonylpiperazide, N-α-(2,4,6-triisopropylphenylsulfonyl)-3-hydroxyguanidino-(D,L)-phenylalanine-4-ethoxycarbonylpiperazide, N-α-(2,4,6-triisopropylphenylsulfonyl)-3-hydroxyguanidino-(L)-phenylalanine-4-ethylaminocarbonylpiperazide (WX-685), N-α-(2,4,6-triisopropylphenylsulfonyl)-3-hydroxyguanidino-(D)-phenylalanine-4-ethylaminocarbonylpiperazide, N-α-(2,4,6-triisopropylphenylsulfonyl)-3-hydroxyguanidino-(D,L)-phenylalanine-4-ethylaminocarbonylpiperazide, benzylsulfonyl-(D)-Ser-Gly-(4-hydroxyguanidinobenzyl)amide (WX-678), 4-chlorobenzylsulfonyl-(D)-Ser-N-Me-Ala-(4-hydroxyguanidinobenzyl)amide, 4-chlorobenzylsulfonyl-(D)-Ser-Gly-(4-hydroxyguanidinobenzyl)amide, benzylsulfonyl-(D)-Ser-N-Me-Gly-(4-hydroxyguanidinobenzyl)amide, 4-chlorobenzylsulfonyl-(D)-Ser-Ala-(4-hydroxyguanidinobenzyl)amide, and also salts thereof, for example the hydrogen sulfates such as, for example, WX-671.HSO$_4$.

The compounds of the invention may be used, where appropriate, together with suitable pharmaceutical adjuvants or carriers for the preparation of medicaments. Administration is possible here in combination with other active compounds, for example other urokinase inhibitors, such as, for example, antibodies and/or peptides, or else with chemotherapeutics and cytostatics or/and cytostatic active compounds.

The medicaments may be administered to humans and animals topically, rectally or parenterally, for example intravenously, subcutaneously, intramuscularly, intraperitoneally, sublingually, nasally or/and inhalationally, for example in the form of tablets, coated tablets, capsules, pellets, suppositories, solutions, emulsions, suspensions, liposomes, inhalation sprays or transdermal systems such as plasters, and particularly preferably orally, for example as a slow-release/retard formulation.

The compounds of the invention are suitable for controlling diseases associated with pathological overexpression of uPA or/and urokinase plasminogen-activator receptor (uPAR). For example, they are capable of inhibiting in a highly efficient manner the growth or/and the spreading of malignant tumors and metastasizing of tumors. Examples thereof are neoplastic disorders, for example breast cancer, lung cancer, cancer of the bladder, stomach cancer, cervix cancer, ovarian cancer, renal cancer, prostate cancer and soft tissue sarcomas, in particular tumors associated with a high rate of metastasizing. The compounds may be used, where appropriate, together with other tumor agents or with other types of treatment, for example radiation or/and surgical procedures.

The compounds of the invention are furthermore also active for other uPA-associated or/and uPAR-associated disorders. Examples of such disorders are, for example, pulmonary hypertension and/or cardiac disorders (e.g. WO 02/00248), disorders of the stomach and intestine, such as, for example, inflammatory bowel disease, premalignant colon adenomas, inflammatory disorders such as, for example, septic arthritis, osteoarthritis, rheumatoid arthritis, or other disorders such as osteoporosis, cholesteatoma, disorders of the skin and the eyes and also viral or bacterial infections, with reference being made explicitly to the disorders mentioned in EP-A-0 691 350, EP-A-1 182 207 and U.S. Pat. No. 5,712,291.

The compounds of the general formula I may be prepared, for example, as in the synthesis schemes in FIGS. 1, 2 and 3.

The compounds of the general formulae II and III may be prepared, for example, as in the synthesis schemes in FIGS. 4 and 6.

uPA inhibitors of the invention are preferably characterized in that they have a bioavailability which is at least 5 times, preferably 10 times, and particularly preferably 100 times, higher than that of the corresponding urokinase inhibitors of this class which have a nonmodified amidino or guanidino function, after oral administration.

Surprisingly, it was found that the uPA inhibitors of the invention have not only improved bio-availability but also a distinctly improved activity to a primary tumor.

The inventive substances of the formulae I, II and III may be used alone or in combination with other physiologically active substances, for example with radiotherapeutics or with cytotoxic or/and cytostatic agents, for example chemotherapeutics, such as, for example, cisplatin, doxorubicin, 5-fluorouracil, taxol derivatives, or/and other chemotherapeutic agents, for example selected from the group consisting of alkylating agents, antimetabolites, antibiotics, epidophyllotoxins and vinca alkaloids. A combination with radiotherapy or/and surgical interventions is also possible.

The invention provides a process for inhibiting urokinase in living organisms, in particular humans, by administering an active amount of at least one compound of the general formula I, II or/and III. The dose to be administered depends on the type and severity of the disorders to be treated. The daily dose, for example, is in the range from 0.01-100 mg/kg active substance.

Finally, the invention relates to novel inhibitors of the urokinase plasminogen activator of the general formulae I, II and III.

BRIEF DESCRIPTION OF THE DRAWINGS

The following figures and the examples are intended to illustrate the invention in more detail.

DETAILED DESCIPTION OF THE INVENTION

EXAMPLES

Example 1

Preparation of WX-671

1.1 N-Acetyl-3-cyano-(D/L)-phenylalanine

Figure 1:
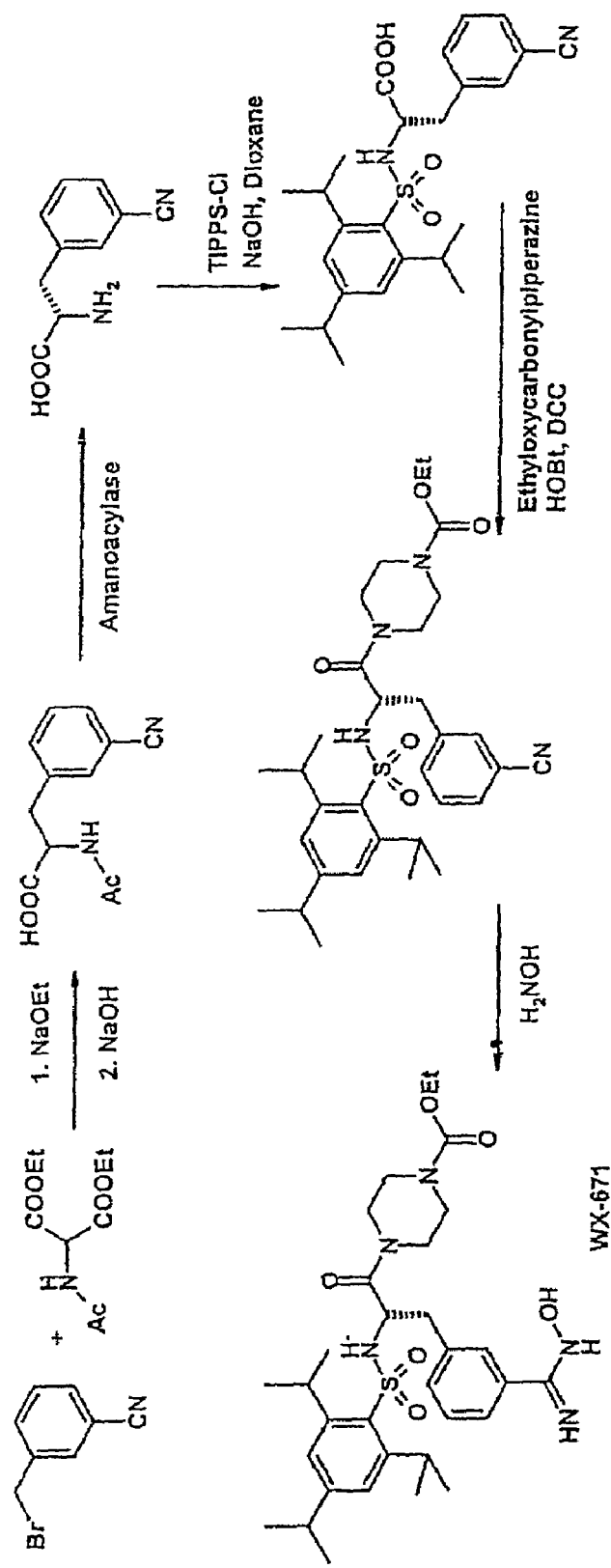
FIGS. 1-4 and 6 depict diagrammatically the preparation of compounds WX-671 (FIGS. 1 and 2), WX-683 (FIG. 3) and WX-678 (FIGS. 4 and 6).
Figure 2:
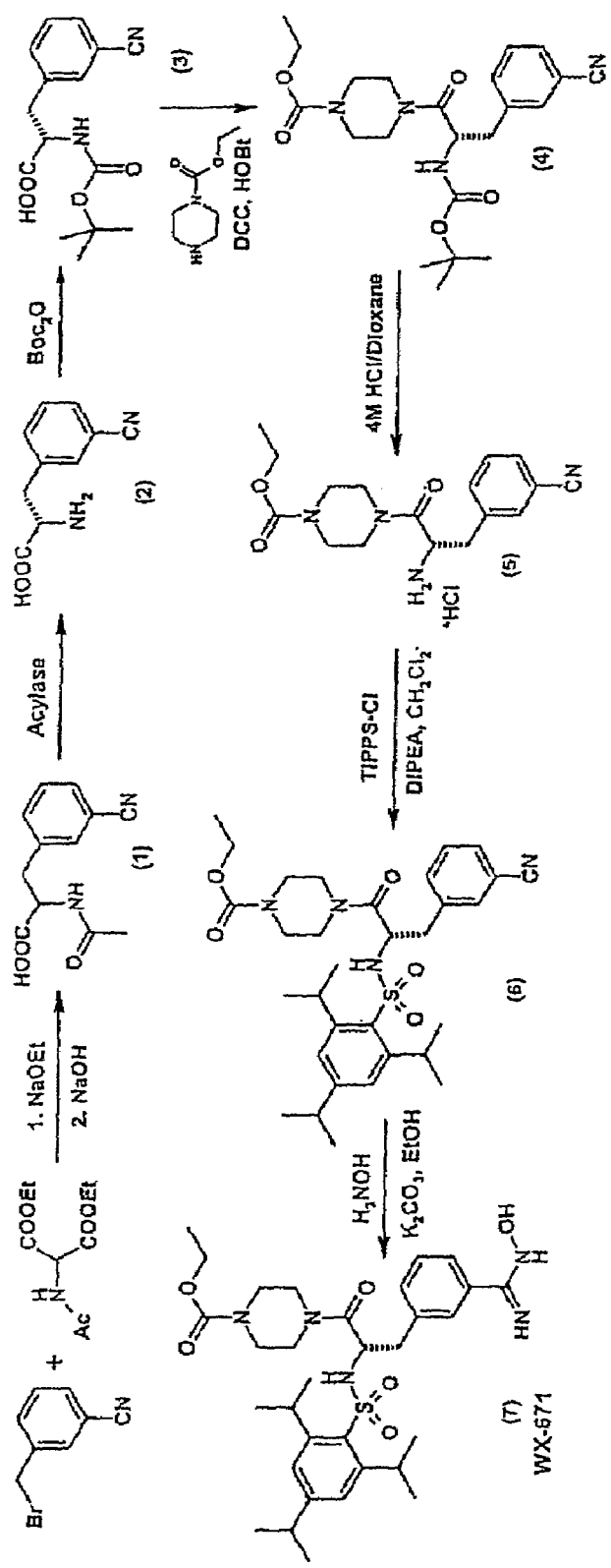
Figure 3:
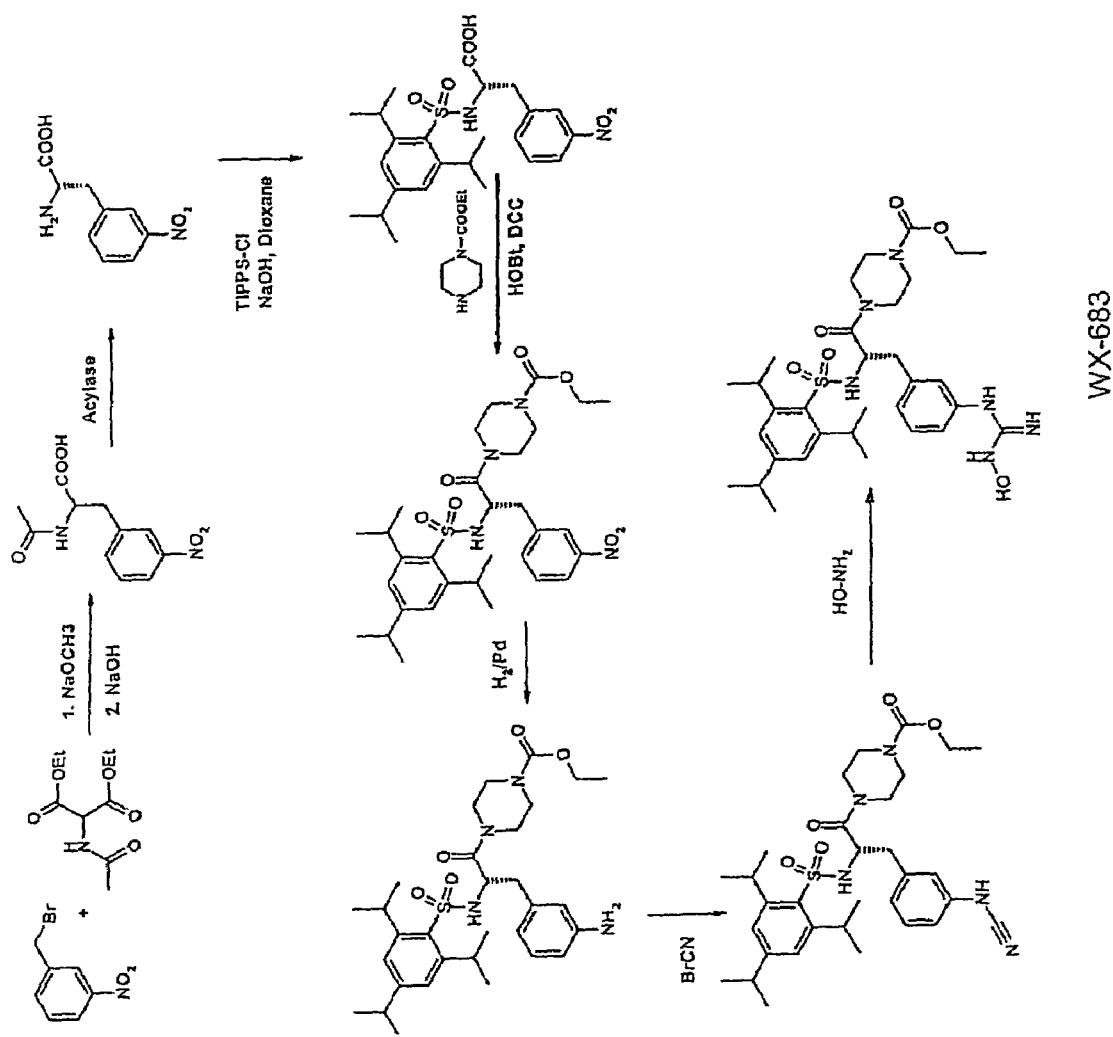
Figure 4:
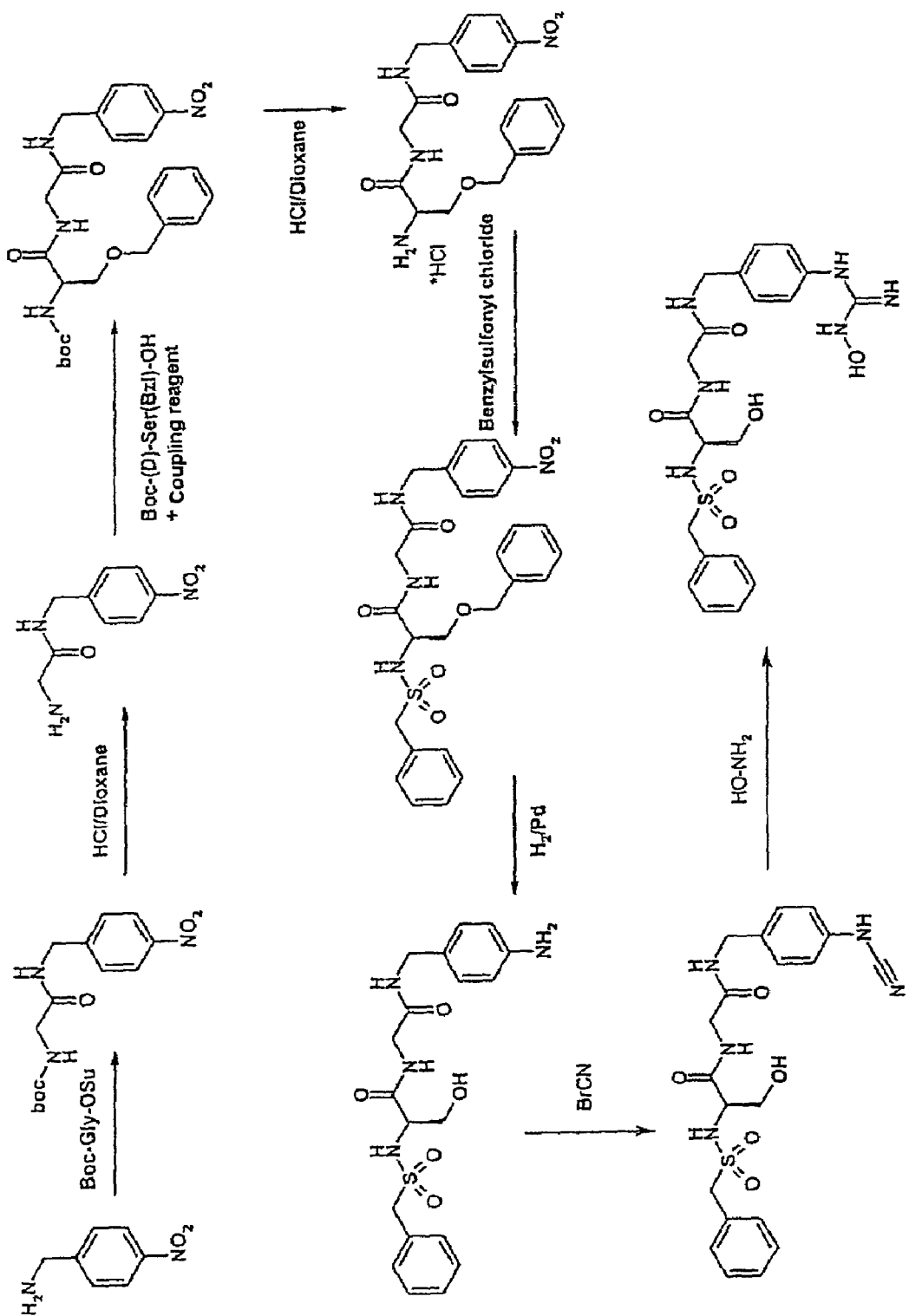

3-Cyanobenzyl bromide (935 g; 4.77 mol), diethyl acetamidomalonate (1036 g; 4.77 mol) and potassium iodide (20 g) were dissolved in 5 l of dioxane at 98° C. under argon and stirred for 5 h. Subsequently, a solution of sodium ethoxide (340 g; 5 mmol) in 2 l of ethanol was added dropwise over a period of 3 h. This was followed by adding 4.4 l of 3M NaOH and stirring at 98° C. for another 2 h and then at room temperature (RT) overnight. The solution was concentrated to ~2 l under vacuum, 3 l of distilled water were added and the solution was cooled to RT. Adjusting the pH to >9 was followed by extracting 3× with 1 l of ethyl acetate. The aqueous phase was adjusted to pH 1 with 4M HCl (approx. 4 l of 4M HCl) and extracted 4× with 1.2 l of ethyl acetate. The combined organic phases were washed with saturated NaCl, the solvent was evaporated and the residue was recrystallized from ethyl acetate.

Yield 815 g (3.5 mol) 73%

1.2 3-Cyano-(L)-phenylalanine (Resolution of the Racemates)

N-Acetyl-3-cyano-(D/L)-phenylalanine (696 g; 3 mol) was dissolved in 2 l of water and 3 l of 1M NaOH, the pH was adjusted to 7.2 with approx. 10 ml of 4M HCl and the solution was heated to 37° C. After adding 28 g of acylase l (Aspergillus Melleus), the solution was stirred slowly at 37° C. for 60 h. After filtration of the resulting precipitate (product), the solution was concentrated to a volume of approx. 1.5 l and the precipitate was filtered off. The combined filter cakes were suspended in 0.5 l of water, stirred, filtered again and dried under vacuum.

Yield 190 g (33%), purity 99% (HPLC)

1.3 Triisopropylphenylsulfonyl (TIPPS)-3-cyano-(L)-phenylalanine

3-Cyano-(L)-phenylalanine (133 g, 700 mmol) was dissolved in 1.2 l of dioxane and 1540 ml of 1M NaOH and cooled to 5° C. Triisopropylphenylsulfonyl chloride (TIPPS-Cl) (212 g; 700 mmol) was dissolved in 1 l of dioxane and added dropwise over a period of 1 h. This was followed by adding more TIPPS-Cl and NaOH and stirring until the reactants were no longer detectable. The orange solution was acidified to pH 5 with 4M HCl and extracted 2× with MTBE. The combined organic solutions were extracted 2× with NaCl solution and the solvent was then evaporated under vacuum and toluene was then added and evaporated in a rotary evaporator.

Yield 302 g (88%) with 93% purity (HPLC)

1.4 TIPPS-3-cyano-(L)-phenylalanine-4-ethoxycarbonylpiperazide

TIPPS-3-cyano-(L)-phenylalanine (215 g; 0.435 mmol; 93% purity), ethyloxycarbonylpiperazine (68.8 g; 0.435 mmol) and 1-hydroxybenzotriazole (13.3 g; 0.087 mol) were dissolved in 650 ml of DMF and cooled to 10° C. A solution of dicyclohexylcarbodiimide (98.7 g; 0.478 mol) in 216 ml of DMF was added dropwise over a period of 2 h and the reaction solution was stirred at RT overnight. After evaporating the solvent, the residue was dissolved in 436 ml of MTBE, the precipitate was filtered off, and the organic solution was extracted in each case 2× with 5% $KHSO_4$, 5% $NaHCO_3$ and distilled water. The solvent was evaporated under vacuum, toluene was added and then evaporated in a rotary evaporator and the product was dried under vacuum.

Yield 261 g of light-yellow solid (90%) with 90% purity (HPLC)

1.5 TIPPS-3-hydroxyamidino-(L)-phenylalanine-4-ethoxycarbonylpiperazide (WX-671)

TIPPS-3-cyano-(L)-phenylalanine-4-ethoxycarbonylpiperazide (130 g; 196 mmol; 90% purity), hydroxylamine hydrochloride (22 g; 313 mmol) and triethylamine (63 g; 626 mmol) were dissolved in 470 ml of ethanol and stirred at RT for 1 day. After evaporating the solvent, the residue was taken up in 300 ml of ethyl acetate and extracted in each case 2× with 5% $KHSO_4$, 5% $NaHCO_3$ and distilled water. After evaporating the solvent, the crude product was dried under vacuum and then recrystallized from ethyl acetate/ether.

Yield 63 g (50%) of white powder with 97% purity (HPLC)

Example 2

Preparation of WX-678

2.1 H-Gly-4-Nitrobenzylamide hydrochloride

4-Nitrobenzylamine hydrochloride (1 g; 5.3 mmol) and diisopropylethylamine (1.8 ml; 10.6 mmol) were dissolved in 70 ml of dichloromethane at RT. BOC-Gly-OSu (1.44 g; 5.3 mmol) was added and the solution was stirred at RT overnight. After evaporating the solvent in a rotary evaporator, the residue was taken up in 50 ml of ethyl acetate and extracted in each case 2× with 5% $KHSO_4$, 5% $NaHCO_3$ and distilled water. The organic phase was dried over $Na_2SO_4$, the solvent was evaporated and toluene was then added and evaporated in a rotary evaporator. The resultant oil was dissolved, without further work-up, directly in 15 ml of 4M HCl/dioxane and stirred at RT. After a short time, the product starts to precipitate. After 1 h, the solvent was evaporated, the solid was suspended in 100 ml of ethyl acetate, filtered off and washed with petroleum ether. The white solid was dried under vacuum.

Yield 1.17 g (90%)

2.2 Fmoc-(D)-Ser(tBu)-Gly-4-nitrobenzylamide

H-Gly-4-nitrobenzylamide hydrochloride (1.17 g; 4.77 mmol), Fmoc-(D)-Ser (tBu)-OH (1.83 g; 4.77 mmol) and diisopropylethylamine (2.5 ml; 14.3 mmol) were dissolved in 40 ml of DMF:dichloromethane 1:1. After adding PyBOP (2.73 g; 5.25 mmol), the solution was stirred at RT. After 2.5 h, the solvent was completely evaporated under high vacuum and the residue was dissolved in 300 ml of dichloromethane and extracted 2× with TIPPS-3-amino-(L)-phenylalanine4-ethoxycarbonylpiperazide and 1× with conc. NaCl. The organic phase was dried over $Na_2SO_4$, the solvent was evaporated and toluene was then added and evaporated in a rotary evaporator. The product was dried under high vacuum.

2.3 H-(D)-Ser(tBu)-Gly-4-nitrobenzylamide hydrochloride

Fmoc-(D)-Ser(tBu)-Gly-4-nitrobenzylamide (3.1 g) was suspended in 100 ml of dichloromethane and 5 g of piperazinomethyl polystyrene resin (=5.5 mmol of piperazine) were added. There was still no reaction after 1 h, and 5 mmol of diisopropylethylamine (856 µl) were added. There was still no reaction after one day, and diisopropylethylamine (5 mmol; 856 µl) was again added and the suspension was concentrated in a rotary evaporator to approx. 20% of the original volume. After 5 days, approx. 50% of product had formed, diisopropylethylamine (5 mmol; 856 µl) was again added and the solution was admixed with 20 ml of DMF in order to improve solubility. After a further 6 days, the resin was filtered off and the solvent was evaporated. The remaining oil was treated with petroleum ether in an ultrasound bath and decanted off. The process was repeated using diethyl ether, in order to remove the byproduct dibenzofulvene. The oil was subsequently dissolved in 30 ml of dichloromethane and the product was precipitated as hydrochloride, using a solution of 2 ml of 4M HCl/dioxane in 20 ml of dichloromethane. The precipitation was completed using 50 ml of petroleum ether, the supernatant was decanted off and the precipitate was dried under vacuum.

Yield 1.68 g of light-yellow powder (90% for the last two stages of synthesis)

2.4 Benzylsulfonyl-(D)-Ser(tBu)-Gly-4-nitrobenzylamide 1.68 g of H-(D)-Ser(tBu)-Gly4-nitrobenzylamide hydrochloride (4.32 mmol) and diisopropylethylamine (2.22 ml; 12.96 mmol) were dissolved in 80 ml of dichloromethane. Addition of benzylsulfonyl chloride (824 mg; 4.32 mmol) was followed by stirring at RT. After 3.5 h, benzylsulfonyl chloride (100 mg) and diisopropylethylamine (500 µl) were again added in order to complete the reaction. After another 2 h, the solvent was evaporated, the residue was taken up in 130 ml of ethyl acetate, the solution was extracted in each case 2× with 5% $NaHCO_3$ and 5% $KHSO_4$ and 1× with concentrated NaCl. The organic phase was dried over $Na_2SO_4$, the solvent was evaporated and toluene was then added and evaporated in a rotary evaporator. The product was dried under high vacuum.

Yield 1.85 g of light-yellow powder (84%)

2.5 Benzylsulfonyl-(D)-Ser(tBu)-Gly-4-aminobenzylamide 1.85 g of benzylsulfonyl-(D)-Ser(tBu)-Gly-4-nitrobenzylamide (3.65 mmol) were dissolved in 50 ml of methanol and hydrogenated over Pd/C. After 8 h, the catalyst was filtered off, the solvent was evaporated, toluene was then added and evaporated in a rotary evaporator and the crude product was dissolved in a little dichloromethane. When the solvent was removed in a rotary evaporator, the product frothed up and solidified under vacuum.

Yield 1.6 g of light-yellow powder (92%)

2.6 Benzylsulfonyl-(D)-Ser-Gly4-aminobenzylamide hydrochloride

In order to remove the tert-butyl protective group, benzylsulfonyl-(D)-Ser (tBu)-Gly-4-aminobenzylamide (1 g) was suspended in 20 ml of 4M HCl/dioxane and stirred at RT. After 7 h, the solvent was evaporated under vacuum, toluene was then added and evaporated in a rotary evaporator and the product was dried under vacuum.

Yield 1.07 g of highly pure product (quantitative)

2.7 Benzylsulfonyl-(D)-Ser-Gly-4-cyanoaminobenzylamide

Benzylsulfonyl-(D)-Ser-Gly-4-aminobenzylamide hydrochloride (500 mg; 1.09 mmol), sodium acetate (224 mg; 2.725 mmol) and cyanogen bromide (127 mg; 1.2 mmol) were dissolved in absolute ethanol dried over a molecular sieve, and stirred at RT for 3 h. The solution was cooled in an ice bath and the precipitated salts were filtered off. The solution was used directly in the next reaction step.

2.8 Benzylsulfonyl-(D)-Ser-Gly-4-hydroxyguanidinobenzylamide

Hydroxylamine hydrochloride (83.4 mg; 1.2 mmol) and diisopropylethylamine (195 µl; 1.2 mmol) were added to the ethanolic crude product solution of benzylsulfonyl-(D)-Ser-Gly-4-cyanoaminobenzylamide and the reaction mixture was stirred at 0° C. overnight. The precipitated salts were filtered off and the solvent was evaporated. The product was purified over prep. reversed phase HPLC.

Yield 120 mg (0.25 mmol; 21%); purity (HPLC): 95%; ESI-MS: m/z=479.0

(M+H$^+$); calculated for $C_{20}H_{26}N_6O_6S_1$: 478

Example 3

Preparation of WX-683

3.1 N-Acetyl-3-nitro-(D/L)-phenylalanine

3-Nitrobenzyl bromide (1000 g; 4.63 mol), diethyl acetamidomalonate (1005 g; 4.63 mol) and potassium iodide (20 g) were dissolved in 4 l of dioxane at 98° C. under argon and stirred for 5 h. Subsequently, a solution of sodium ethoxide (340 g; 5 mmol) in 2 l of ethanol was added dropwise over a period of 3 h. This was followed by adding 550 g of NaOH (13.75 mol) and stirring at 98° C. for another 2 h and then at RT overnight. The solution was concentrated to ~2 l under vacuum, 3 l of distilled water were added and the solution was cooled to RT. Adjusting the pH to >9 was followed by extracting 3× with 1 l of ethyl acetate. The aqueous phase was adjusted to pH 1 with 4M HCl (approx. 4 l of 4M HCl) and extracted 4× with 1.2 l of ethyl acetate. The combined organic phases were washed with saturated NaCl, the solvent was evaporated and the residue was recrystallized from ethyl acetate.

Yield 1011 g (3.2 mol) 69%

3.2 3-Nitro-(L)-phenylalanine (Resolution of the Racemates)

N-Acetyl-3-nitro-(D/L)-phenylalanine (1000 g; 3.17 mol) was dissolved in 2 l of water and 3 l of 1M NaOH, the pH was adjusted to 7.2 with approx. 10 ml of 4M HCl and the solution was heated to 37° C. After adding 28 g of acylase l (Aspergillus Melleus), the solution was stirred slowly at 37° C. for 60 h. After filtration of the resulting precipitate (product), the solution was concentrated to a volume of approx. 1.5 l and the precipitate was filtered off. The combined filter cakes were suspended in 0.5 l of water, stirred, filtered again and dried under vacuum.

Yield 245 g (37%), purity 99% (HPLC)

3.3 TIPPS-3-nitro-(L)-phenylalanine

3-Nitro-(L)-phenylalanine (210 g, 1 mol) was dissolved in 1.2 l of dioxane and 500 ml of 4M NaOH and cooled to 5° C. TIPPS-Cl (363 g; 1.2 mol) was dissolved in 1 l of dioxane and added dropwise over a period of 1 h. This was followed by adding more TIPPS-Cl and NaOH and stirring until the reactants were no longer detectable. The orange solution was acidified to pH 5 with 4M HCl and extracted 2× with MTBE. The combined organic solutions were extracted 2× with NaCl solution and the solvent was then evaporated under vacuum and toluene was then added and evaporated in a rotary evaporator.

Yield 427 g (68%) with 76% purity (HPLC)

3.4 TIPPS-3-nitro-(L)-phenylalanine-4-ethoxycarbonylpiperazide

TIPPS-3-nitro-(L)-phenylalanine (210 g; 0.44 mmol; 76% purity), ethyloxycarbonylpiperazine (69.7 g; 0.44 mmol) and 1-hydroxybenzotriazole (101 g; 660 mmol) were dissolved in 650 ml of DMF and cooled to 10° C. A solution of dicyclohexylcarbodiimide (100 g; 0.484 mmol) in 216 ml of DMF was added dropwise over a period of 2 h and the reaction solution was stirred at RT overnight. After evaporating the solvent, the residue was dissolved in 436 ml of MTBE, the precipitate was filtered off, and the organic solution was extracted in each case 2× with 5% $KHSO_4$, 5% $NaHCO_3$ and distilled water. The solvent was evaporated under vacuum, toluene was added and then evaporated in a rotary evaporator and the product was dried under vacuum.

Yield 278 g of a brown resin (70%) with 69% purity (HPLC)

3.5 TIPPS-3-amino-(L)-phenylalanine-4-ethoxycarbonylpiperazide

TI PPS-3-nitro-(L)-phenylalanine-4-ethoxycarbonylpiperazide (157 g; 176 mmol) was dissolved in 800 ml of ethanol, admixed with 19.7 g of 10% palladium on activated carbon catalyst and hydrogenated for 3 days by slowly passing through hydrogen. After filtering off the catalyst, the solvent was evaporated under vacuum and the crude product was chromatographically purified over silica gel.

Yield 21 g (38%) with 95% purity (HPLC)

3.6 TIPPS-3-cyanamido-(L)-phenylalanine-4-ethoxycarbonylpiperazide

TIPPS-3-amino-(L)-phenylalanine-4-ethoxycarbonylpiperazide (14.6 g; 24.9 mmol), sodium acetate (anhydrous) (5.11 g; 62.2 mmol) and cyanogen bromide (2.9 g; 27.4 mmol) were dissolved in ethanol and the solution was stirred at RT for 10 h. After evaporating the solvent, the residue was taken up in ethyl acetate and the solution was extracted with 5% $KHSO_4$, 5% $NaHCO_3$ and distilled water. After evaporating the solvent, the crude product was purified chromatographically over silica gel.

Yield 10 g (60%) with 92% purity 3.7 TIPPS-3-hydroxyguanidino-(L)-phenylalanine4-ethoxycarbonylpiperazide (WX-683)

TIPPS-3-cyanamido-(L)-phenylalanine-4-ethoxycarbonylpiperazide (9.3 g; 15 mmol), hydroxylamine hydrochloride (1.15 g; 16.5 mmol) and diisopropylethylamine (3.87 g; 30 mmol) were dissolved in ethanol and the solution was stirred at RT overnight. After evaporating the solvent, the product was purified chromatographically over silica gel.

Yield 3.87 g (39%) purity 98% (HPLC)

Example 4

In Vivo Assay of the uPA Inhibitor Prodrug WX-671 with Regard to Tumor Spreading, Tumor Growth and Metastasizing in Rats Breast Cancer Model Fragments of 10-25 $mm^3$ of the BN472 breast cancer (Kort et al., J. Natl. Cancer Inst 72, 709-713, 1984) from a donor animal were implanted underneath the fatty body of a mammary gland of groups (n=15 per group) of female brown Norwegian rats aged 7-8 weeks. The treatments started 72 h after tumor implantation and were repeated daily until the animals were sacrificed after 30 days. The control group (A) received 0.75 ml of the substance-free substance carrier solution consisting of 5% ethanol, 5% D-mannitol and 5% Tween 20 in water orally by gavage. The treatment groups (B and C) received, orally by gavage, either 1 mg/kg (group B) or 5 mg/kg (group C) WX-671 in a volume of 0.75 ml of substance carrier solution. The comparative group D received 1 mg/kg WX-UK1 dissolved in 5% D-mannitol by intraperitoneal injection.

Growth of the inoculated tumors was determined in the dimensions length and width twice weekly, using a slide gauge. After the animals had been sacrificed, the therapy end points, tumor weight, weights of the axillary and intraperitoneal lymph nodes and also the number of macroscopic lung metastases were determined.

Summary of the Results

Figure 5:
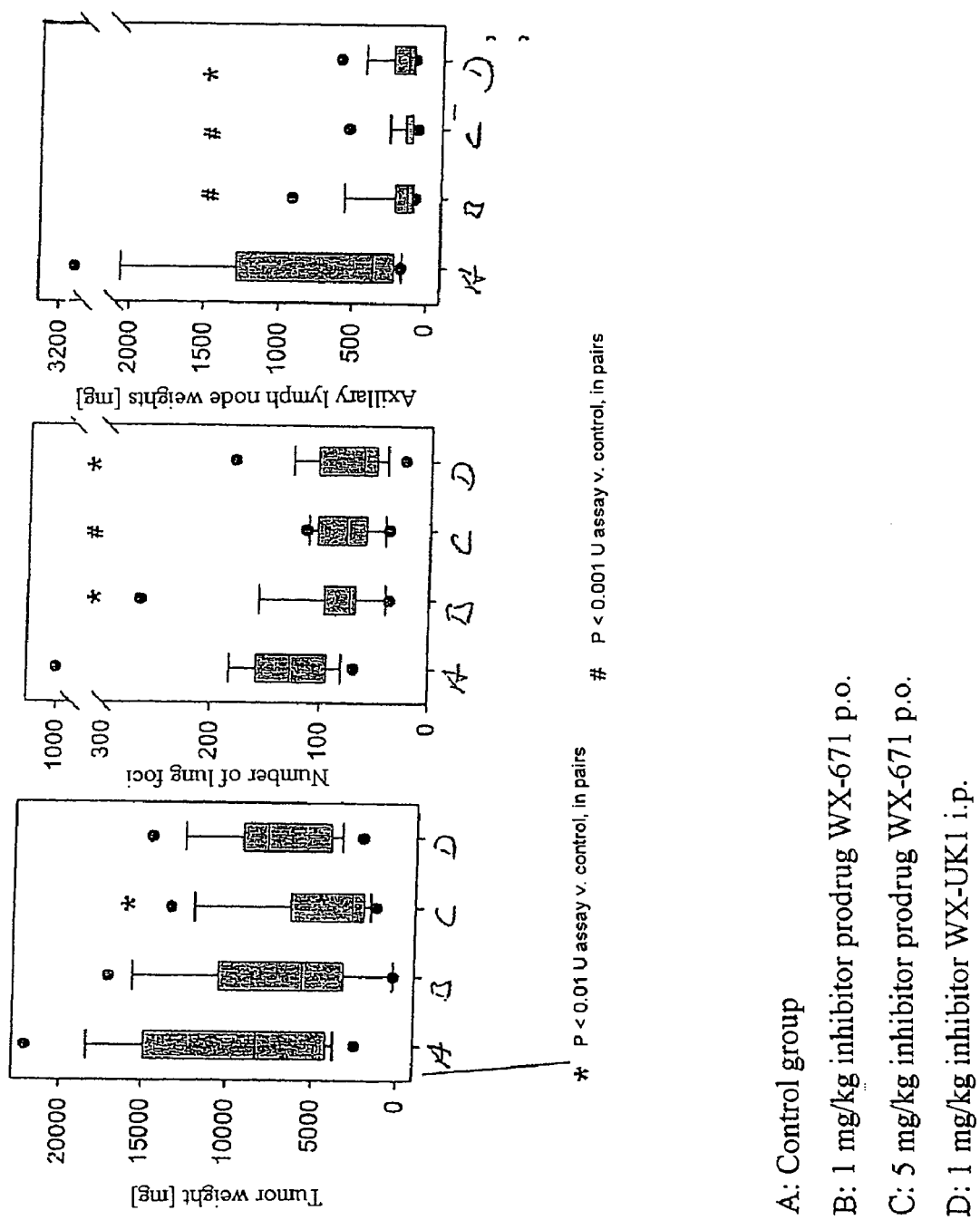
FIG. 5 depicts results in the rat breast cancer model with the substance of the invention, WX-671, in comparison with controls.
Figure 6:
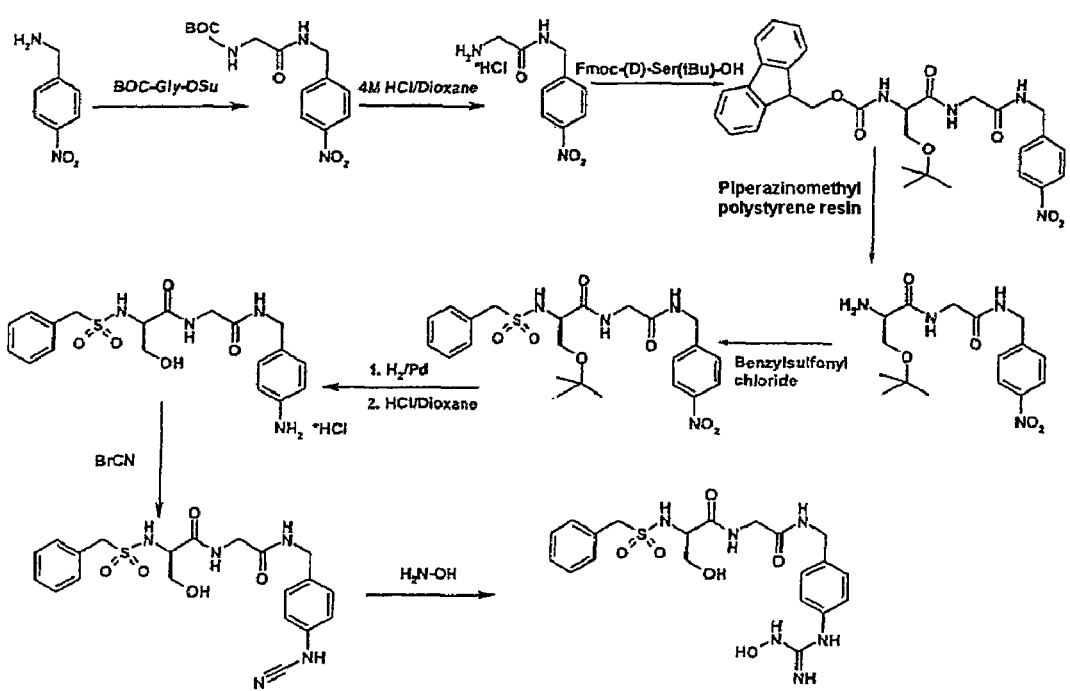

In all experiments, treatment with WX-671 achieved a considerable reduction in the size and, respectively, the weight of the tumors and in the number and, respectively, mass of metastases, in comparison with the control group. In the mammary tumor model, the average tumor weights at the end of the treatment were reduced in the WX-671-treated group by more than 66% (p.o.) compared to the control, while an i.p. treatment with the comparative inhibitor substance WX-UK1 achieved only a reduction by approx. 5%. The number of lung foci in the inhibitor prodrug-treated groups was reduced by more than 42% (p.o.) and the average weights of the axillary lymph nodes by more than 63% (p.o.) (FIG. 5).

The development of bodyweight increase and the comparison of organ weights between inhibitor- and vehicle-treated groups gave no indication of a possible considerable toxicity of the inhibitor under the conditions described.

Example 5

Preparation and Characterization of WX-671 Hydrogen Sulfate

Preparation 6.0 g of the free base WX-671 were dissolved in 50 ml of acetone. 1.25 molar equivalents of $H_2SO_4$ were added undiluted. The mixture was stirred at room temperature for 2 h. The hydrogen sulfate crystallized from the solution. After removing the solvent, the remaining white solid was dried under vacuum.

Characterization

The solubility of the hydrogen sulfate in water at 25° C. was 1172.5 mg/l (calculated for the base). The purity was ≧98% (area % after HPLC).

5 g of hydrogen sulfate were stirred in 25 ml of water/acetone (80/20) for 7 days, filtered and dried at room temperature for 60 h. The stoichiometry measured showed that the salt was stable to dissociation. After stirring, no increase in the content of organic contaminations was found (determination by HPLC).

After storage as a solid substance at 90° C. for 1 week, <1.5% organic contaminations were found (determination by HPLC).

On the basis of the results above, the hydrogen sulfate has excellent suitability for the preparation of pharmaceutical preparations.

Example 6

In Vivo Test of the UPA Inhibitor WX-683 on Tumor Development, Tumor Growth and Metastasis in the Rat Breast Cancer Model BN-472 breast cancer fragments of approximately 20 mm in diameter were taken from a female donor animal. The tumor was excised, separated from the adhering connective tissue, rinsed with saline, and resuspended in HAM-F12 cell culture medium (Invitrogen BV, Breda, Netherlands), supplemented with 10% fetal calf serum (Hi Clone, Greiner BV, Alphen a/d Rijn, Netherlands). The tumor cortex was sliced into cubes of about 2 mm side length and implanted orthotopically under the mammary fat pad of the 4$^{th}$ right nipple of 7 to 9-weeks old recipient female BN rats. Of the grafted tumors, over 95% became palpable within 3 days, and metastasis to the lungs were detected within 2 to 4 weeks.

Figure 7:
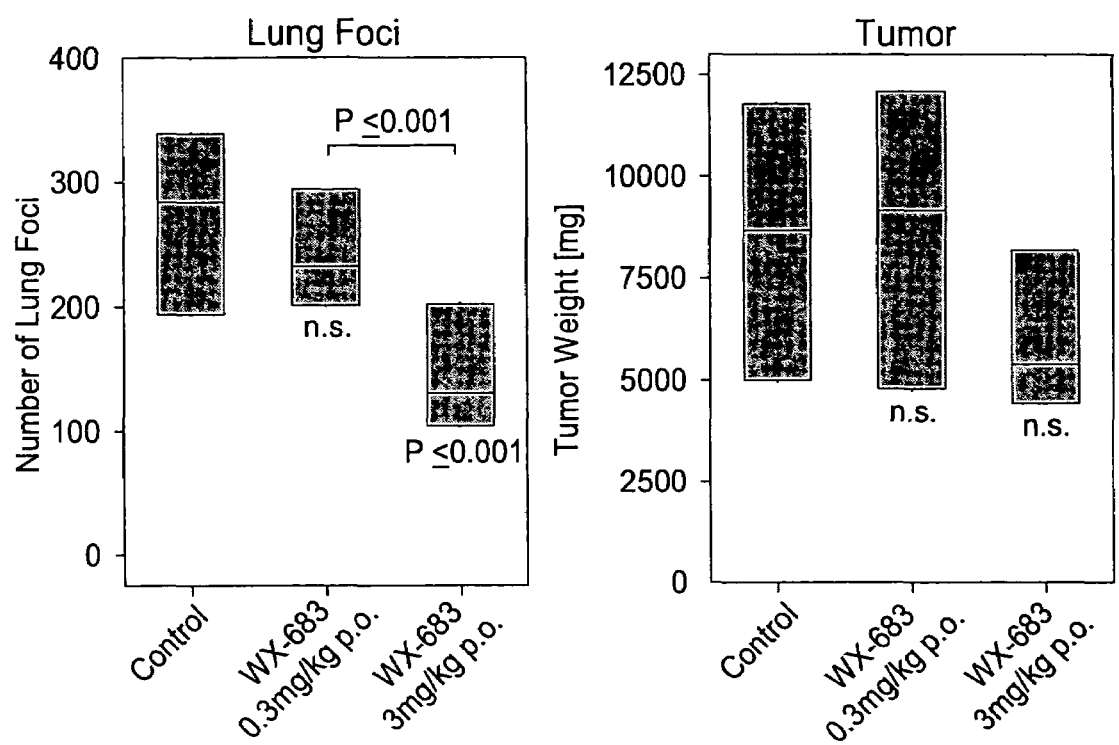
FIG. 7. WX-683 was administered orally at doses of 0.3 and 3 mg/kg/day. The median number of lung metastases was reduced dose dependently by 18% and 54%, respectively. The median primary tumor weight was reduced by 38% at the highest dosage used. Boxes represent the interquartile ranges with the median value shown as a line within the box; P values below boxes designate the significance levels of treatment groups vs vehicle control as calculated with the Mann-Whitney rank sum test with pairwise comparison. P values >0.05 were regarded as statistically not significant (n.s.).

Shortly before starting the WX-683 treatment on day 3 after tumor transplantation, all rats were individually weighed and the size of the individual tumor measured as the product of the two largest perpendicular diameters. They were then assorted into groups consisting of 18 rats. The rats were pre-selected such that all treatment groups had similar average body weights and tumor size distributions at the start of the treatment. Control rats received 800 µl vehicle (0.01 N HCl) p.o. WX-683 was dissolved in vehicle at the appropriate concentrations and administered in a volume of 800 µl at dosages of 0.3 and 3 mg/kg by oral gavage once a day. The duration of WX-683 treatment ranged from 24 to 25 days, depending whether the tumor size exceeded the maximum tolerable burden. At the end of the treatment period, the rats were sacrificed, their tumors harvested, separated from the adhering connective tissue and the total tumor weight of every rat was determined. To assess the number of lung metastases, the lungs were fixed in Bouin's solution for at least 24 h. Subsequently the number of lung metastases were determined by counting the yellowish-white macroscopic foci on the lung surface (FIG. 7). This study was approved by the Independent Institutional Animal Care and Use Committee (DEC-Consult), Rotterdam, Netherlands, permit no: Erasmus MC OZP 136-03-01, issued on 01.03.2003.

Example 7

In Vivo Test of the Effectiveness of WX-671 in the Colon Carcinoma Model CC531.

The anti-tumor efficacy of WX-671 was demonstrated using the transplantable rat colon carcinoma CC531. Six to seven week old female animals (n=18 per group, body weight range 100-130 g received from day 3 after tumor inoculation onwards 0.03, 0.3 or 3.0 mg/kg of WX-671. Control animals received the vehicle (5% ethanol, 5% Tween2o, 5% D-mannitol in water). Seven weeks after tumor implantation the animals were killed and evaluated with respect to primary tumor weight and metastatic endpoints.

The final median tumor weight in treatment groups versus vehicle group was unchanged in the group receiving WX-671 at 0.03 mg/kg, reduced non-significantly by 6% in the group receiving WX-671 at 0.3 mg/kg and significantly (p=0.015) reduced by 15% in the group treated with 3 mg/kg. The difference between terminal tumor sizes in the 0.3 mg/kg groups and the 3.0 mg/kg group was not significant, however. Regarding metastatic endpoints the median number of macroscopic lung foci was significantly reduced (P<0.0001) by 37%, 64% and 57% relative to control in the treatment groups receiving 0.03, 0.3 and 3.0 mg/kg, respectively. The median intraperitoneal lymph node weights were reduced by 31%, 41% and 46% relative to control in the three treatment groups, the latter two reductions being statistically significant (P<0.001).

Figure 8:
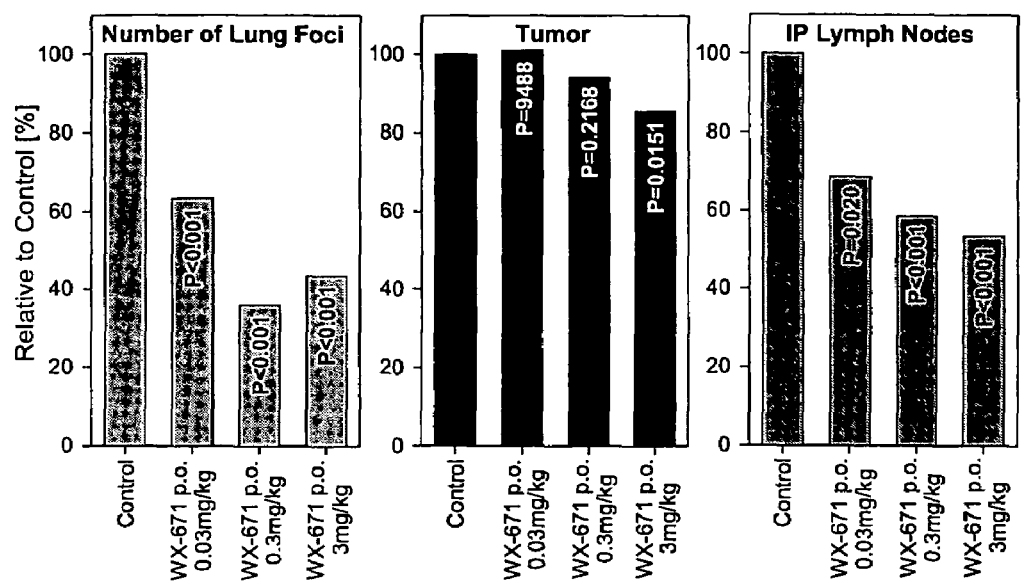
FIG. 8: Medians of tumor endpoints as determined after 7 weeks of incubation of CC531 rat colon tumor growing subcutaneously under WX-671 therapy at the indicated doses or treated with vehicle. P-values of the significance level of the difference of the medians in the treatment groups compared with control are indicated in the bars.

Medians of tumor endpoints and significance levels (pair-wise comparison) of the difference of medians in the treatment versus vehicle control groups are depicted in FIG. 8. A highly significant reduction of the number of macroscopic lung foci was apparent in all treatment groups with the lowest dose (0.03 mg/kg, reduction by 37%) being the least efficacious. At 0.3 mg/kg the effect was maximum (reduction by 64%) and was not improved (reduction by 57%) in the group receiving WX-671 at the ten-fold dose i.e. 3.0 mg/kg. A similar pattern was apparent regarding the weights of intraperitoneal lymph nodes. Median weight reductions were achieved by 31% at 0.03 mg/kg (non-significant) and 41% and 46% at the medium and high dose level, respectively.

Example 8

In Vivo Test of the Effectiveness of WX-671 in the Pancreatic Adenocarcinoma Model CA20948

The anti-tumor efficacy of WX-671 was assayed in a metastatic rat pancreatic tumor model, CA20948. Groups of eighteen rats were inoculated with tumor by intraperitoneal injection of a tumor cell suspension, prepared from a solid tumor harvested from a donor rat.

Figure 9:
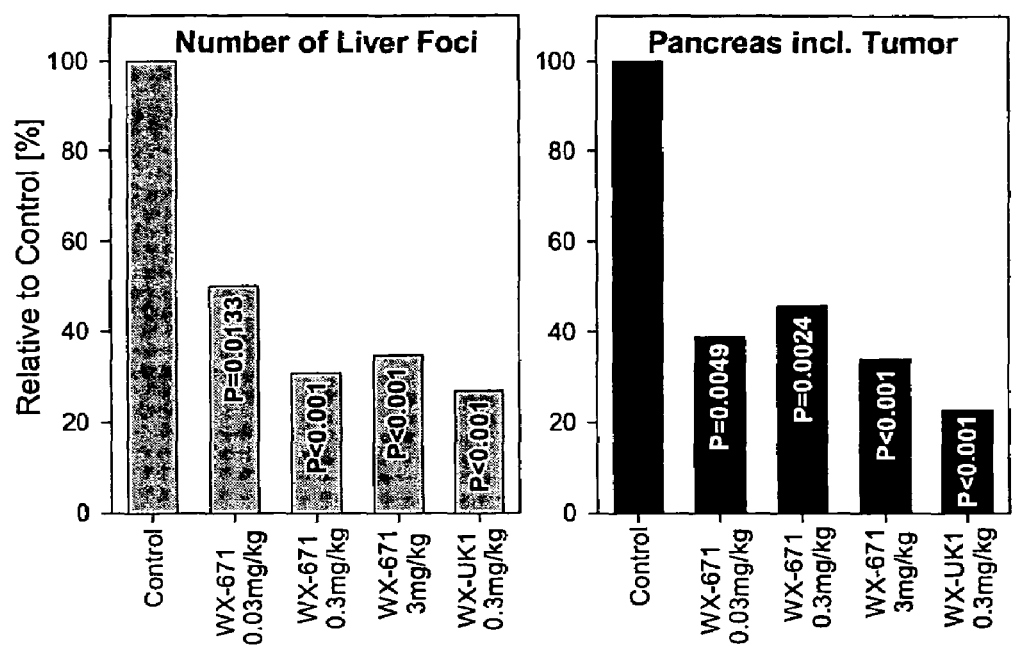
FIG. 9: Medians of tumor-related endpoints as determined in the vehicle control group and after treatment with various dose levels of WX-671 in the CA20948 rat syngeneic pancreatic tumor model. Intraperitoneally administered WX-UK1 at 0.3 mg/kg once daily was assayed in parallel as a positive control. P-values of the difference of medians in the control groups compared with treatment groups (pairwise comparison) as calculated with Mann-Whitney-U-test are indicated in the individual bars.

In this model the intraperitoneally grafted cells migrate to the pancreas to form a pancreatic tumor intimately associated with the pancreas. Within 3 weeks the tumor disseminates typically to the liver to form metastatic lesions which can be counted. Treatments at dose levels of 0.03, 0.3 and 3.0 mg/kg once daily were orally applied daily from day 3 onwards. One group received vehicle as a control and one group received 0.3 mg/kg of WX-UK1 by intraperitoneal injection. FIG. 9 shows medians and P-values of the relevant final tumor endpoints of this model as found 3 weeks after inoculation of the tumor.

Table 1 lists the respective percentage reduction of median tumor endpoints relative to control. All treatment schedules had a highly significant effect on the final intraperitoneally grafted tumor plus pancreas mass and on the number of macroscopic liver foci compared with control. Reduction of liver metastasis seemed to be dose dependent.

To assess whether the treatments would have influence not only on liver foci counts but also on the growth rate of metastatic lesions, the relative abundance of large metastases (>2 mm) in the various groups was assessed. The percentage of large liver foci was determined by dividing the number of large lesions by the number of total lesion detected on the livers. Results are listed in Table 1. In the vehicle group the percentage of large metastases was 30.7% whereas in the treatment groups the percentage of large liver lesions was uniformly smaller. This indicates that the treatments with WX-671 (and WX-UK1) not only reduced the number of liver foci but may have also had an inhibitory activity on the growth rate of the metastatic lesions.

TABLE 1

Percentage of the number of large (>2 mm) metastatic liver lesion of the total number of liver lesions in the various treatment groups.

| CA20948 pancreatic tumor | percentage large mets |
|---|---|
| Vehicle control | 30.7% |
| WX-671 0.03 mg/kg | 12.4% |
| WX-671 0.3 mg/kg | 16.2% |
| WX-671 3.0 mg/kg | 20.4% |
| WX-UK1 0.3 mg/kg | 13.4% |

The anti-tumor efficacy of intraperitoneal WX-UK1 at 0.3 mg/kg was similar as the efficacy of oral WX-671 at the same dose or higher.

Example 9

Bio-Availability of WX-671 after Oral Administration in Rat and Rhesus Monkey Single Dose Kinetics of Oral WX-671 in Rat The pharmacokinetics of WX-671 in rat was investigated with SD rats (n=3 per time point) using oral doses of 3 and 9 mg/kg solubilized in 10 ml/kg of 1.7% Tween20, 1.7% ethanol and 5% of D-mannitol. Table 2 lists pharmacokinetic parameters as calculated with WinNonlin pharmacokinetics software. The bioavailability in rat of WX-671 was 34.5% and 42.1% at doses of 3 and 9 mg/kg, respectively, making reference to single dose plasma kinetics after intravenous injection of 3 mg/kg of WX-671.

TABLE 2

Descriptive pharmacokinetic parameters after oral and intravenous administration of WX-671 from bio-availability study in rat as calculated with WinNonlin 4.0.1 from Pharsight.

| | oral WX-671 3 mg/kg WX-671 in plasma | oral WX-671 9 mg/kg WX-671 in plasma | intravenous WX-671 3 mg/kg WX-671 in plasma |
|---|---|---|---|
| $AUC_{24h}$ [min*ng/ml] | 45 192 | 161 117 | 135 303 |
| $AUC_{inf}$ [min*ng/ml] | 45 279 | 161 824 | 136 354 |
| $C_{max}$ [ng/ml] | 551.6 | 963.9 | 3277.0 |
| $T_{max}$ [min] | 30 | 60 | 4 |
| $T_{1/2}$ [min] | 176 | 230 | 702 |
| Cl [l/min/kg] | 0.07 | 0.06 | 0.02 |
| $V_D$ [l/kg] | 16.9 | 30.12.99 | 22.3 |

Single Oral Dose Plasmakinetics of WX-671 in Rhesus Monkey

The single dose plasmakinetics of WX-671 following oral gavage of WX-671 was determined in Rhesus monkeys (n=3) at a dose of 15 mg/kg of WX-671 p.o. Table 3 lists pharmacokinetic parameters calculated with WinNonlin software from plasma kinetics of both analytes using the non-compartmental analysis option. Bioavailability was calculated making reference to intravenous WX-671 at 3 mg/kg.

TABLE 3

Descriptive pharmacokinetic parameters (plasma) after oral and intravenous administration of WX-671 from bioavailability study in Rhesus monkey as calculated with WinNonlin 4.0.1 from Pharsight

| | oral WX-671 15 mg/kg WX-671 | intravenous WX-671 3 mg/kg WX-671 |
|---|---|---|
| $AUC_{24h}$ [min ng/ml] | 52 618 | 59 782* |
| $AUC_{inf}$ [min ng/ml] | 53 082 | 59 809 |
| $C_{max}$ [ng/ml] | 222 | 1995 |
| $T_{max}$ [min] | 180 | 1 |
| $T_{1/2}$ [min] | 441 | 84 |
| Cl [l/min/kq] | 0.28 | 0.05 |
| $V_D$ [l/kg] | 180 | 6.1 |

*extrapolated by WinNonlin, last timepoint 960 min

Example 10

Determination of the Pharmacokinetics in the Oral Administration of WX-671 in Humans An open label phase I study to investigate the bioavailability and pharmacokinetics of oral WX-671 given at four dose levels pre- and post-prandially to healthy male subjects was carried out. The study drug was available as hard gelatine capsules containing WX-671 hydrogen sulphate equivalent to 50 mg or 200 mg WX-671 free base.

Study design: WX-671 as hydrogen sulphate was administered orally at four escalating dose levels (50, 100, 200 and 400 mg free base) to four volunteers per group as a single dose pre-prandially. One week later each subject received the same dose post-prandially with a standardized breakfast to compare the effect of food on the pharmacokinetics of the drug Study objectives: Safety was assessed by clinical observations, vital signs, ECG measurements and extensive safety laboratory data. In addition, effects on diuresis/saliuresis were monitored.

Pharmacokinetics: plasma concentrations of WX-671 were measured.

Study Results and Conclusions:
At all dose levels tested WX-671 was well tolerated as judged from the assessment of vital signs, electrocardiogram (ECG), general safety laboratory and coagulation data and adverse event profiles.

The coagulation parameters prothrombin time (PT) and activated partial thromboplastin time (aPTT) remained within normal ranges during and after WX-671 administration.

Saliuresis: No difference in saliuresis between the different dose groups was noted.

Maximum plasma concentrations and the area under the curve (AUC) increase overproportionally between the dose groups.

Intake with food (post-prandial administration) generally resulted in larger AUCs with the exception of the lowest dose group where pre-prandial intake achieved larger AUCs.

PLASMA PHARMACOKINETICS

In the study healthy volunteers received WX-671 as hydrogen sulphate given as single oral doses corresponding to 50, 100, 200 and 400 mg WX-671 free base. 48 hour plasma profiles were obtained for WX-671. Each subject received two single doses, the first dose was given pre-prandially and the second dose post-prandially with a period of one week between administrations.

Figure 10:
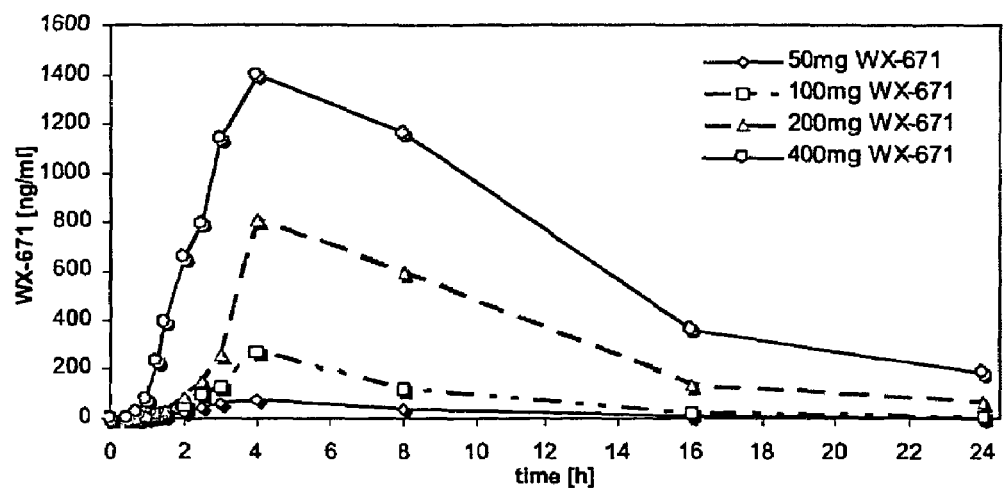
FIG. 10: WX-671 plasma levels of four dose groups after post-prandial administration of WX-671.

Mean pharmacokinetic parameters and individual ranges for the WX-671 prodrug active as determined in the various treatment groups of the study are summarized in Table 4. The corresponding mean plasma profiles of the various dose groups is shown for the post-prandial situation in FIG. 10.

TABLE 4

Mean pharmacokinetic parameters (with individual ranges) for WX-671 after oral dosing to four subjects at each dose.

| Dose (mg) | WX-671 | | | | | | |
|---|---|---|---|---|---|---|---|
| | $c_{max}$ (ng/ml) | $C_{24h}$ (ng/ml) | $AUC_{0\text{-}24h}$ (min ng/ml) | $AUC_{inf}$ (min ng/ml) | $t_{1/2}$ (h) | Cl (l/min) | $V_D$ (l) |
| 50 mg pre-pr. | 167.3 (11.8-259.2) | 3.0 (0.8-7.0) | 49 795 (4577-94012) | 51 369 (4955-96738) | 5.6 (3.1-9.3) | 3.2 (0.5-10.1) | 1483 (201.3-4760) |
| 50 mg post-pr. | 97.5 (49.2-149.0) | 2.9 (1.1-4.0) | 33 759 (26644-40179) | 35 862 (29694-43773) | 6.1 (4.1-8.2) | 3.0 (1.1-7.6) | 736.4 (581.3-829.0) |
| 100 mg pre-pr. | 428.2 (177.9-725.5) | 8.5 (3.7-11.6) | 125 786 (56826-203003) | 132 417 (64302-211820) | 6.0 (5.1-7.3) | 1.0 (0.5-1.6) | 544.6 (208.9-858.0) |
| 100 mg post-pr. | 270.2 (247.8-333.0) | 9.7 (5.5-16.3) | 109 918 (90183-136424) | 116 752 (95708-149815) | 5.8 (4.3-6.5) | 0.9 (0.7-1.0) | 445.4 (326.8-562.9) |
| 200 mg pre-pr. | 661.7 (288.8-991.3) | 18.2 (5.7-31.2) | 211 839 (105549-345179) | 226 549 (115380-362972) | 6.0 (5.3-7.6) | 1.1 (0.6-1.7) | 562.1 (257.0-793.5) |
| 200 mg post-pr. | 963.2 (613.3-1850.2) | 69.6 (21.9-167.4) | 442 097 (205859-818948) | 497 435 (268097-955328) | 5.7 (4.8-6.6) | 0.5 (0.2-0.7) | 243.1 (119.1-376.5) |
| 400 mg pre-pr. | 1 833 (1238.6-2600.2) | 91.4 (60.6-130.8) | 800 563 (490280-1282960) | 873 071 (546015-1387685) | 5.9 (4.7-6.8) | 0.5 (0.3-0.7) | 259.0 (154.5-373.7) |
| 400 mg post-pr. | 1 578 (940.5-1930.4) | 184.2 (110.1-267.6) | 954 538 (520712-1285640) | 1 097 297 (604223-1498381) | 5.7 (5.2-6.4) | 0.4 (0.3-0.7) | 199.4 (143.0-325.3) |

The invention claimed is:

1. A pharmaceutical composition, which comprises, as an active compound, one or more compounds of the formula

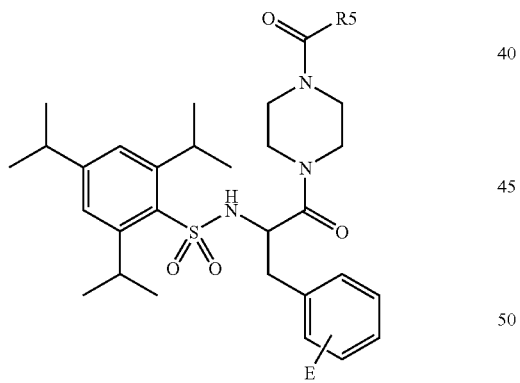

in which E is a group

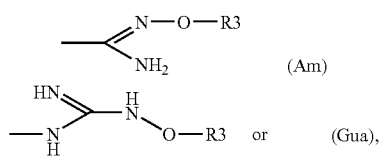

$R^3$ is —H, $R^5$ is —OR$^6$, —N(R$^6$)$_2$, —C$_1$-C$_6$-alkyl, —C$_2$-C$_6$-alkenyl or —C$_2$-C$_6$-alkynyl, said alkyl, alkenyl and alkynyl moieties being straight-chained or branched and being unsubstituted or substituted by at least one substituent selected from the group consisting of halogen, —OR$^6$, —OCOR$^6$, —N(R$^6$)$_2$, —NR$^6$COR$^6$, —NR$^6$CON(R$^6$)$_2$, COOR$^6$, and a radical selected from the group consisting of a cycloalkyl-, aryl-, and bicyclic-radical which is unsubstituted or substituted by at least one substituent selected from the group consisting of —C$_1$-C$_3$-alkyl, —C$_1$-C$_3$-alkoxy, halogen, —OR$^6$, =O, —NO$_2$, —CN, —COOR$^6$, —N(R$^6$)$_2$, —NR$^6$COR$^6$, —NR$^6$CON(R$^6$)$_2$ and —OCOR$^6$, $R^6$ is —H, —C$_1$-C$_6$-alkyl, —C$_2$-C$_6$-alkenyl or —C$_2$-C$_6$-alkynyl, or a radical selected from the group consisting of a cycloalkyl-, aryl-, and bicyclic-radical which is unsubstituted or substituted by at least one substituent selected from the group consisting of —C$_1$-C$_3$-alkyl, —C$_1$-C$_3$-alkoxy, halogen, —OR$^6$, =O, —NO$_2$, —CN, —COOR$^6$, —N(R$^6$)$_2$, —NR$^6$COR$^6$, —NR$^6$CON(R$^6$)$_2$ and —OCOR$^6$, said alkyl, alkenyl and alkynyl moieties being straight-chained or branched and being unsubstituted or substituted by at least one substituent selected from the group consisting of halogen, —OR$^6$, —OCOR$^6$, —N(R$^6$)$_2$, —NR$^6$COR$^6$, —NR$^6$CON(R$^6$)$_2$, COOR$^6$, and a radical selected from the group consisting of a cycloalkyl-, aryl-, and bicyclic-radical which is unsubstituted or substituted by at least one substituent selected from the group consisting of —C$_1$-C$_3$-alkyl, —C$_1$-C$_3$-alkoxy, halogen, —OR$^6$, =O, —NO$_2$, —CN, —COOR$^6$, —N(R$^6$)$_2$, —NR$^6$COR$^6$, —NR$^6$CON(R$^6$)$_2$ and —OCOR$^6$, or a salt of said compound and a pharmaceutically customary carrier, diluent or/and adjuvant.

2. The pharmaceutical composition of claim 1, wherein said active compound is selected from the group consisting of
N-α-(2,4,6-triisopropylphenylsulfonyl)-3-hydroxyamidino-(L)-phenylalanine-4-ethoxycarbonylpiperazide,
N-α-(2,4,6-triisopropylphenylsulfonyl)-3-hydroxyamidino-(D)-phenylalanine-4-ethoxycarbonylpiperazide, N-α-(2,4,6-triisopropylphenylsulfonyl)-3-hydroxyamidino-(D,L)-phenylalanine-4-ethoxycarbonylpiperazide, N-α-(2,4,6-triisopropylphenylsulfonyl)-3-hydroxyguanidino-(L)-phenylalanine-4-ethoxycarbonylpiperazide, N-α-(2,4,6-triisopropylphenylsulfonyl)-3-hydroxyguanidino-(D)-phenylalanine-4-ethoxycarbonylpiperazide, N-α-(2,4,6-triisopropylphenylsulfonyl)-3-hydroxyguanidino-(D,L)-phenylalanine-4-ethoxycarbonylpiperazide, N-α-(2,4,6-triisopropylphenylsulfonyl)-3-hydroxyguanidino-(L)-phenylalanine-4-ethylaminocarbonylpiperazide, N-α-(2,4,6-triisopropylphenylsulfonyl)-3-hydroxyguanidino-(D)-phenylalanine-4-ethylaminocarbonylpiperazide, and N-α-(2,4,6-triisopropylphenylsulfonyl)-3-hydroxyguanidino-(D,L)-phenylalanine-4-ethylaminocarbonylpiperazide, or a physiologically compatible salt thereof;

and a pharmaceutically acceptable carrier, diluent or/and adjuvant.

3. The pharmaceutical composition as claimed in claim 1, wherein the composition is in an orally administrable form.

4. The pharmaceutical composition as claimed in claim 1, wherein the compound is present as a sulfate or hydrogen sulfate salt.

5. The pharmaceutical composition as claimed in claim 2, in which the compound is N-α-(2,4,6-triisopropylphenylsulfonyl)-3-hydroxyamidino-(L)-phenylalanine-4-ethoxycarbonylpiperazinium hydrogen sulfate or N-α-(2,4,6-triisopropylphenylsulfonyl)-3-hydroxyamidino-(L)-phenylalanine-4-ethoxycarbonylpiperazinium sulfate.

6. A salt of a compound of the formula I,

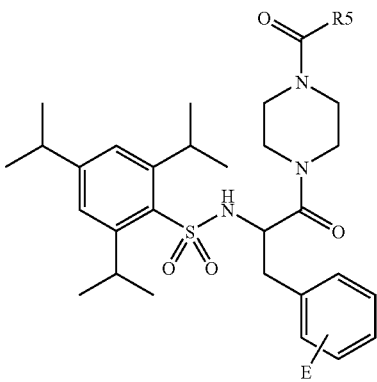

in which E is

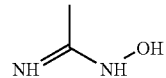

and R5 is ethoxy and wherein the salt is in the form of a hydrogen sulfate or sulfate.

* * * * *